United States Patent
Stecklein et al.

(10) Patent No.: US 7,560,082 B2
(45) Date of Patent: Jul. 14, 2009

(54) STERILIZATION WRAPS AND METHODS FOR STERILIZING ARTICLES

(75) Inventors: Greg Stecklein, Lake Villa, IL (US); Michael Duski, Wheeling, IL (US); James F. Whitaker, Alexander, NC (US); Debra Schotz, Wilmette, IL (US); Barbara Anne Blankenship, El Paso, TX (US); Alejandro Puentes, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 227 days.

(21) Appl. No.: 10/966,354

(22) Filed: Oct. 13, 2004

(65) Prior Publication Data
US 2005/0163654 A1    Jul. 28, 2005

Related U.S. Application Data

(63) Continuation-in-part of application No. 10/685,545, filed on Oct. 14, 2003.

(51) Int. Cl.
*A61L 2/00* (2006.01)
*A61L 9/00* (2006.01)

(52) U.S. Cl. .................. 422/294; 422/292; 422/26; 422/28

(58) Field of Classification Search ............... 422/294, 422/292
See application file for complete search history.

(56) References Cited

U.S. PATENT DOCUMENTS 2,899,799 A    6/1959    Korpman (Continued)

FOREIGN PATENT DOCUMENTS

EP    0 307 173    3/1989

(Continued)

OTHER PUBLICATIONS

U.S. Appl. No. 09/862,473, filed Sep. 20, 2001, Weiss et al.

(Continued)

*Primary Examiner*—Elizabeth L McKane
*Assistant Examiner*—Regina Yoo
(74) *Attorney, Agent, or Firm*—Arent Fox LLP.

(57) ABSTRACT

There is provided an improved sterilization wrap and a method for using the improved sterilization wrap to sterilize an article. The wrap is made of at least a first panel of sterilization material and includes an additional panel of material. The first panel is multi-layered and includes at least one pathogen filtration layer. The first panel is rectangular and has an outer periphery and a central portion. The outer periphery includes first, second, third and fourth edges. The additional panel of material is bonded to the first panel, approximately at a forty-five degree angle to the first panel, with a substantial portion of the additional panel being adjacent to the central portion of the first panel. The perimeter of the additional panel is smaller than the perimeter of the first panel. Portions of the additional panel are bonded to the first panel along the first, second, third and fourth edges of the first panel. The article to be sterilized is placed on the additional panel, is wrapped, and sterilant is applied to the wrapped article. A chemical visual indicator is provided to indicate whether or not the article has been exposed to adequate sterilization conditions.

14 Claims, 9 Drawing Sheets

U.S. PATENT DOCUMENTS

| | | | |
|---|---|---|---|
| 3,704,096 A | 11/1972 | Verses et al. | |
| 3,780,857 A * | 12/1973 | Rosano et al. | 206/370 |
| 3,930,580 A | 1/1976 | Bazell et al. | |
| 4,091,921 A | 5/1978 | Lewis | |
| 4,206,844 A | 6/1980 | Thukamoto et al. | |
| 4,342,392 A | 8/1982 | Cox | |
| 4,382,063 A | 5/1983 | Romito et al. | |
| 4,514,361 A | 4/1985 | Hirsch | |
| 4,579,715 A | 4/1986 | Bruso | |
| 4,596,696 A | 6/1986 | Scoville, Jr. | |
| 4,636,472 A | 1/1987 | Bruso | |
| 4,692,307 A | 9/1987 | Bruso | |
| 4,705,171 A | 11/1987 | Eldridge | |
| 4,902,478 A | 2/1990 | Hambleton | |
| 4,918,003 A | 4/1990 | Macaro et al. | |
| 5,200,147 A | 4/1993 | Augurt | |
| 5,204,062 A | 4/1993 | Buglino et al. | |
| 5,217,901 A | 6/1993 | Dyckman | |
| RE34,515 E | 1/1994 | Foley | |
| 5,435,971 A | 7/1995 | Dyckman | |
| 5,478,749 A | 12/1995 | Dyke | |
| 5,524,755 A | 6/1996 | Deeds | |
| 5,549,868 A * | 8/1996 | Carlson, II | 422/1 |
| 5,635,134 A | 6/1997 | Bourne et al. | |
| 5,688,476 A * | 11/1997 | Bourne et al. | 422/294 |
| 5,804,512 A | 9/1998 | Lickfield et al. | |
| 5,942,438 A | 8/1999 | Antonoplos et al. | |
| 5,958,337 A | 9/1999 | Bourne et al. | |
| 6,051,187 A | 4/2000 | Hughes | |
| 6,406,764 B2 * | 6/2002 | Bayer | 428/35.2 |
| 6,440,375 B1 * | 8/2002 | Davis et al. | 422/300 |
| 6,517,916 B1 | 2/2003 | Bayer et al. | |
| 6,630,104 B1 | 10/2003 | Bayer et al. | |

FOREIGN PATENT DOCUMENTS

| | | |
|---|---|---|
| EP | 0 370 835 | 5/1990 |
| EP | 0 754 796 | 1/1997 |
| FR | 2 521 906 | 8/1983 |
| GB | 2 360 707 | 10/2001 |
| JP | 11034264 | 2/1999 |

OTHER PUBLICATIONS

PCT US2004/033829 Search Report, Jan. 31, 2005.

USPTO Office Action dated Sep. 17, 2007; U.S. Appl. No. 10/685,545; First Named Inventor, Clay Canady; Filed Oct. 14, 2003.

William A. Rutala, PhD, MPH, and David J. Weber, MD, MPH; May 1, 2000; "Choosing a Sterilization Wrap for Surgical Packs"; ICT Infection Control Today Magazine; http://www.infectioncontroltoday.com/articles/.

* cited by examiner

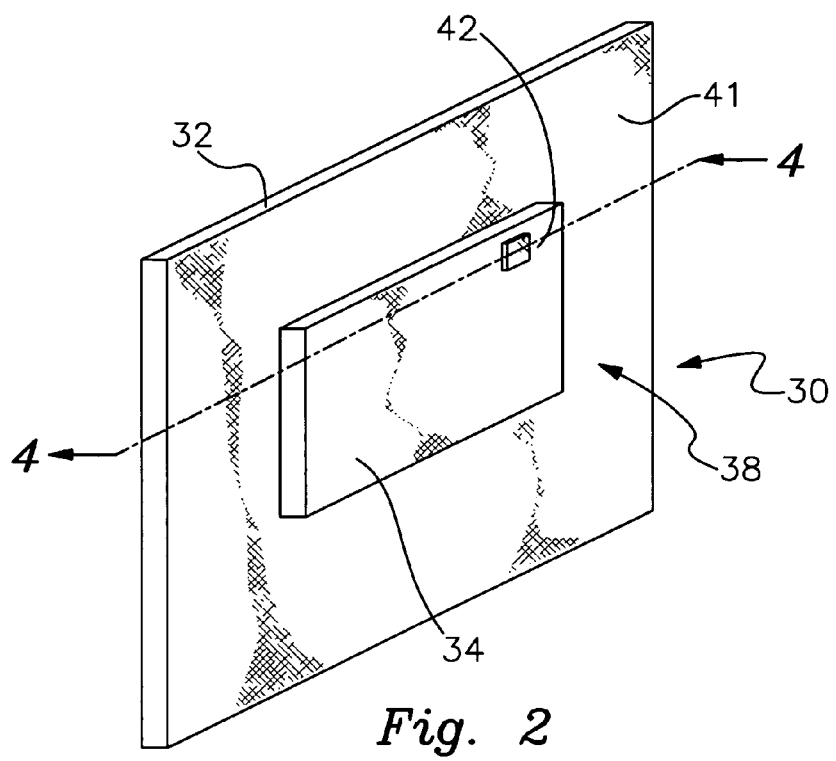
*Fig. 2*
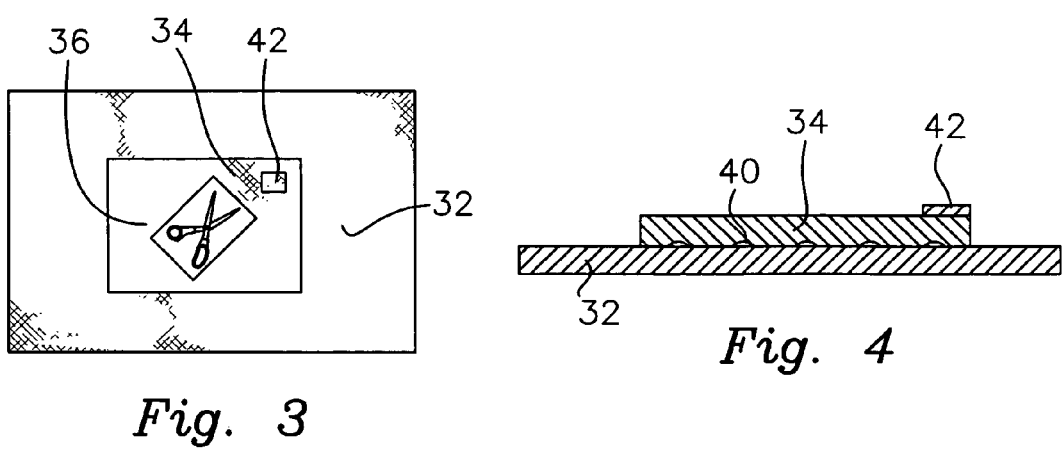
*Fig. 3*                *Fig. 4*

STERILIZATION WRAPS AND METHODS FOR STERILIZING ARTICLES

RELATED APPLICATIONS

This application is a continuation-in-part of U.S. patent application Ser. No. 10/685,545, filed on Oct. 14, 2003, titled IMPROVED STERILIZATION WRAPS AND METHODS FOR STERILIZING ARTICLES.

BACKGROUND OF THE INVENTION

This invention relates to sterilization wrap. More particularly, it relates to sterilization wrap utilizing at least two layers or panels of material.

Reusable medical instruments must be sterilized prior to each use. Normally, these instruments are exposed to a sterilant to achieve sterilization. As used herein, the term sterilant is meant to refer to the sterilization effectors that are conventionally utilized with sterilization wrap, sterilization techniques, including but not limited to steam, ethylene-oxide, plasma, or the like. In order for the instruments to remain sterile after the sterilization procedure, the instruments must be wrapped in a material called sterilization wrap prior to the sterilization procedure.

The most common type of sterilization wrap is a three-ply laminate consisting of a layer of melt blown polypropylene sandwiched between two layers of spun bond polypropylene. The wrap includes bond points all across the face of the material so that the material is held together, i.e., laminated. This three-ply material is commonly referred to as "SMS," which is short for spun bond—melt blown—spun bond. Most hospitals specify SMS as the sterilization wrap to be used because SMS is sufficiently porous to permit steam, ethylene-oxide and other sterilization materials to penetrate through the material to the surgical instruments, but has filtration properties sufficient to prevent the passage of most pathogens therethrough so as to maintain sterility after the sterilization process. The wrap also protects articles during sterilization and acts as a filtration medium for the sterilant.

In most hospitals, there is a protocol which requires surgical instruments to be wrapped with two separate panels of material so that if one panel becomes torn but not discovered, there is a redundancy which will maintain the sterility of the surgical instruments. The wrapping of surgical instruments with two separate panels of sterilization wrap obviously is labor intensive in that the clinician must first place the instruments on one panel of sterilization material and wrap the instruments, and then place the wrapped package on another panel of sterilization material and again wrap the package containing the instruments.

In an attempt to reduce the labor required to provide dual wrapping of surgical instruments, Kimberly-Clark Corporation has developed a product called "One Step® Sterilization Wrap." One Step® Sterilization Wrap is made by bonding two separate panels of sterilization wrap together near two of the edges of the adjacent panels. The Kimberly-Clark One Step® product is described in U.S. Pat. Nos. 5,635,134 and 5,688,476.

FIG. 1 herein shows one of the Kimberly-Clark One Step® products described in these Kimberly-Clark patents. Sterilization wrap 10 includes a top panel 12 made of SMS and a bottom panel 14 also made of SMS. The lengths and widths of top panel 12 and bottom panel 14 are identical and the outside edges of each layer align with one another. The two layers of SMS are bonded together near two opposing edges 16 and 18, as illustrated by bond lines 20 and 22. The method of bonding the two panels together may be ultrasonic bonding. The other two opposing edges 24 and 26 are not bonded together so there is a visible gap 28 between panels 12 and 14 so that the user of the sterilization wrap visually distinguishes the fact that there are, indeed, two panels. Apparently the purpose for ensuring that the two panels are visually distinguishable as separate panels is so that the user knows with certainty that the item to be sterilized has two panel protection. However, because of this gap 28, debris could enter the region between the two panels. With two of the edges being unbonded, it is possible that the panels become misaligned so that if a sharp object penetrates both panels, the resulting holes in each panel could also become misaligned, thus reducing ones ability to determine whether or not there is a hole through both panels. In addition, since edges 24 and 26 are not bonded and bond lines 20 and 22 are somewhat removed from edges 16 and 18, fibers from those edges could become released from the wrap. Also, since the edges 24 and 26 are not bonded, the two panels might be pulled apart by mistake during use. Furthermore, since the wrap shown in FIG. 1 is not sealed right to the edges 16 and 18, the user might perceive that there could be contamination between the panels.

Recently Cardinal Health has introduced a new two panel sterilization wrap called Simul-Wrap® which overcomes the problems of the Kimberly-Clark One Step® product described above. The Simul-Wrap® product is made of two identical panels of SMS sterilization material which are bonded together along all four edges. The Cardinal Health Simul-Wrap® product is shown in U.S. Pat. No. 6,517,916. However, both the One Step® product and the Simul-Wrap® product could be improved.

OBJECT OF THE INVENTION

It is, therefore, the general object of this invention to provide improved sterilization wraps and methods for the use thereof.

SUMMARY OF THE INVENTION

In accordance with one form of this invention, there is provided a sterilization wrap for wrapping an article to be sterilized. A first panel of sterilization material is provided. The first panel is preferably rectangular and has an outer periphery and a central portion. The outer periphery includes first, second, third and fourth edges. An additional panel of material is provided. The additional panel of material is bonded to the first panel. A substantial portion of the additional panel is adjacent to the central portion of the first panel. The perimeter of the additional panel is smaller than the perimeter of the first panel. A portion of the additional panel is bonded to the first panel along the first edge.

In accordance with another form of this invention, there is provided a sterilization wrap for wrapping an article to be sterilized. A first panel of sterilization material is provided. An additional panel of material is provided. The additional panel is attached to the first panel. The first panel is multi-layered and includes at least one pathogen filtration layer. The additional panel does not include a pathogen filtration layer.

In accordance with another form of this invention, there is provided a sterilization wrap for wrapping an article to be sterilized. A first rectangular panel of sterilization material is provided. An additional rectangular panel is provided. The additional panel is bonded to the first panel. The additional panel is oriented on the first panel so as to form a diamond shape with respect to the first panel.

In accordance with still another form of this invention, there are provided methods for sterilizing an article, including the steps of providing an article to be sterilized and wrapping the article to be sterilized with the sterilization wraps described above and applying sterilant to the wrapped article.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 2 is a perspective view of one embodiment of sterilization wrap;

FIG. 3 is a plan view of the sterilization wrap of FIG. 2 with an article to be sterilized received thereon;

FIG. 4 is a sectional view of the sterilization wrap of FIG. 2 taken through section line 4-4.

Figure 1:
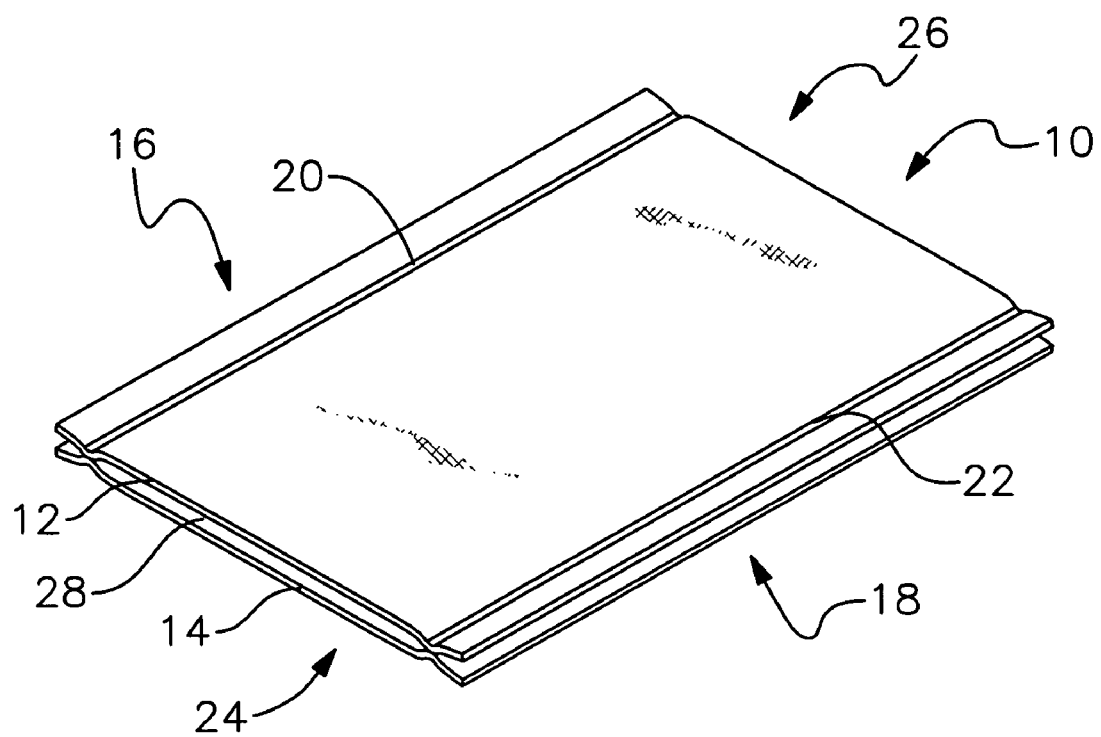
FIG. 1 is a perspective view of a prior art sterilization wrap.

The thicknesses of the materials shown in the drawings have been exaggerated for illustrative purposes and for ease of understanding. In addition, the thicknesses of the bond sites are exaggerated.

DESCRIPTION OF THE PREFERRED EMBODIMENTS

Referring now more particularly to FIG. 2, there is provided sterilization wrap 30 having a first panel or layer 32 and a second or additional layer or panel 34. The first panel or layer 32 may be made of any fibrous or non-fibrous material so long as it can perform the function of sterilization wrap so as to inhibit pathogens from passing therethrough but will permit sterilant such as steam and ethylene to pass therethrough (hereinafter sometimes referred to as "sterilization material"). Preferably, the first layer 32, which is the outside layer, is made of SMS. The material from which the first layer 32 is made is sometimes referred to herein as a panel of sterilization material. The second layer 34, which is the inside layer and which, in the embodiment of FIG. 2 is absorbent, may be made of cellulose or some other absorbent material, which absorbs liquids and aids in drying and which also permits a sterilant, such as steam or ethylene-oxide, to pass therethrough, but inhibits pathogens from passing therethrough. Other absorbent materials could include, but are not limited to, absorbent synthetics such as hydrophillic spunmelt polyolefins, polyester, nylon, as well as polyrayons and bicomponent fibers. The second layer 34 is sometimes referred to herein as a panel of absorbent material. In order to reduce the cost of the sterilization wrap 30 while not reducing its effectiveness, the second or inside layer 34 has a smaller perimeter than the first or outside layer 32. It is preferred that the perimeter of the inside layer 34 be at least 25% less than the outside layer 32.

As can be seen from FIG. 3, the inside layer 34 receives the article to be sterilized 36 thereon. Often the article to be sterilized is a tray containing surgical instruments. Wrapping protocol calls for article to be sterilized 36 to be oriented forty-five degrees with respect to SMS panel 32. While inside layer 34 has a smaller perimeter than outside layer 32, it should be large enough so that when the article to be sterilized 36 is wrapped by sterilization wrap 30, both the bottom and sides of the article to be sterilized 36 is covered by inside layer 34.

Outside layer 32 includes a central portion 38. Inside layer 34 is adjacent to the central portion 38 and is attached to the first panel 32 by means of gluing, ultrasonic bonding or some other form of adherence. Glue spots 40 are illustrated in FIG. 4. Alternatively, inside layer 34 may be made of any fibrous or non-fibrous material, preferably but not limited to SMS or spun bond polypropylene which adds strength but does not have the liquid absorbent properties of cellulose. The structure of inside layer 34 when it is made of SMS is discussed below in reference to FIG. 9. The structure of inside layer 34 when it is made of spun bond polypropylene is discussed below in reference to FIGS. 13-19. In any event, this inside layer provides abuse resistance and containment properties over the prior art sterilization wrap described above.

By reinforcing the area of direct contact under the article to be sterilized 36, the primary point of potential damage to the wrap has been addressed. The method by which trays are wrapped yield several layers of material folds on the top of the article to be sterilized 36. In the event that wrapped articles get stacked on top of one another, thicker and/or heavier inside layer 34 protects the underside of the article 36 while the multiple folds are responsive to contact on the top side of article 36.

As noted, also the inner layer 34 may be made of a moisture absorbent material, such as cellulose, which provides an enhanced moisture absorption function. After the article to be sterilized 36 has been sterilized, in particularly through a steam sterilization process, moisture often remains on the article to be sterilized 36. This moisture enhances the growth of pathogens which may not have been killed during the sterilization process. By using an absorbent material, i.e., absorption material, as the material for layer 34, this moisture tends to be wicked away from the article to be sterilized 36 and more effectively dried. Thus the chances of pathogen growth on or around the article to be sterilized is greatly reduced.

It is preferred that outer layer 32 be of a different color from inner layer 34. Since inner layer 34 is always within the sterile field, this color differential will inform the sterile clinician that it is okay to touch any portion of the sterile field formed by the inside surface of outer layer 32 and inside layer 34.

It is also preferred that a sterilization chemical visual indicator 42, which may also be an integrator or emulator, be adhered to inside layer 34 or to the inside surface 41 of outside layer 32 in the vicinity of inside layer 34. The sterilization indicator could be of a chemistry which meets or exceeds the requirements of Class 1-Class 6 chemical indicators as defined by ISO 11140-1. The sterilization indicator turns color in the presence of steam or ethylene-oxide or other sterilant and will remain at that color after sterilization has taken place. This informs the clinician that the article to be sterilized has, indeed, been exposed to adequate sterilization conditions at the time that the clinician opens the wrapped article.

Sterilization indicators are known and two such indicators are described in U.S. Pat. No. 4,514,361 issued to Hirsch and U.S. Pat. No. 2,889,799 issued to Korpman, which are hereby incorporated herein by reference. Sterilization integrators are known and one such integrator is described in U.S. Pat. No. 4,448,548, which is hereby incorporated herein by reference.

The sterilization wrap described above can be manufactured using conventional equipment and techniques readily available to those skilled in the medical fabric field.

The sterilization wrap described above may be used as set forth below. The article to be sterilized 36, as shown in FIG. 3, is placed on the outside surface of inner layer 34. The article to be sterilized 36 is then wrapped utilizing standard sterilization wrapping techniques so that a portion of the inside layer 34 covers the bottom and sides of the article to be sterilized 36, and a portion of the outside layer 32 also covers the top of the article to be sterilized 36. The wrapped package is then exposed to a sterilization process. The wrapped package is subjected to sterilants, such as steam, ethylene-oxide or plasma, for a predetermined period of time so that substantially all of the pathogens which may be present on the article to be sterilized 36 are killed. The package is then stored for usage. When it is time to use the article to be sterilized 36, the package is unwrapped by the clinician. The sterile clinician will know it is all right to touch the sterile field formed by the inner layer 34 because the inner layer 34 and the outside layer 32 are different colors. The clinician will then observe the status of sterilization indicator, integrator, or emulator 42 to determine whether or not the article 36 has been exposed to adequate sterilization conditions. The article to be sterilized 36 may then be used.

The above-described improved sterilization wrap provides the two layers of protection and ease of use associated with Kimberly-Clark's One Step® and Cardinal Health's Simul-Wrap®, while having the added features of increased protection in the central area adjacent to the article to be sterilized and further providing an ability to wick moisture away from the article to be sterilized, particularly in the case of steam sterilization, and in addition, visually informs the clinician that the inside of the wrap is the sterile field and visually informs the clinician that the article has, indeed, been exposed to adequate sterilization conditions.

While FIGS. 2 through 4 show absorbent layer 34 attached to a single panel of sterilization material, it is preferred that two (2) layers of sterilization material are utilized.

Figure 5:
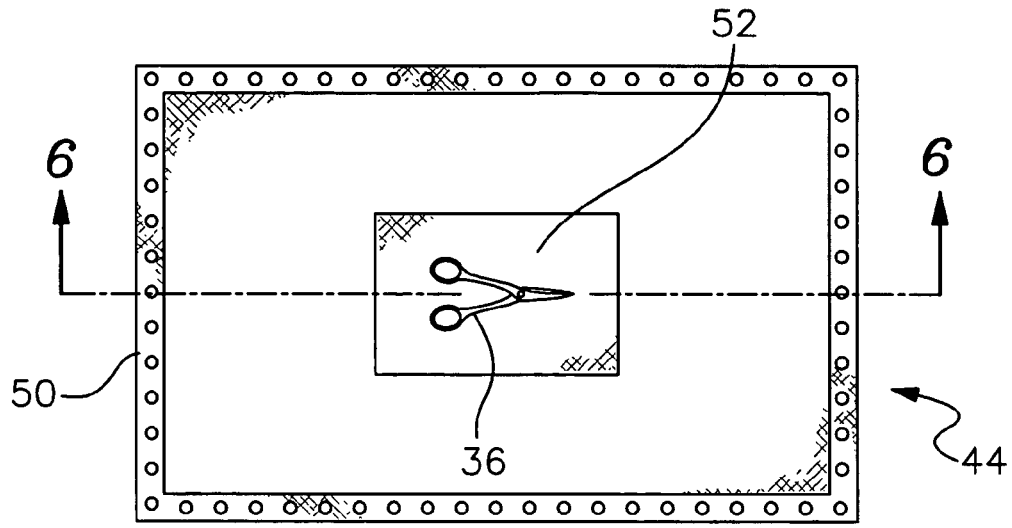
FIG. 5 is a plan view of another embodiment of sterilization wrap.
Figure 6:
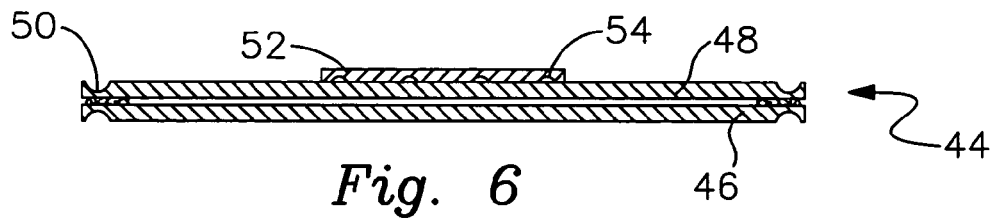
FIG. 6 is a sectional view of the sterilization wrap of FIG. 5 taken through section lines 6-6.

Referring now more particularly to FIGS. 5 and 6, two-layer sterilization wrap 44 is provided and includes outside layer 46 and inside layer 48, each made of sterilization material such as SMS. The two layers 46 and 48 each have four edges 49, 51, 53 and 55 and are bonded together at the four edges about their outer peripheries 50, preferably by heat and pressure. The bonded two-layer sterilization material 44 may be the Simul-Wrap® product which is commercially available from Cardinal Health (1500 Waukegan Road, McGaw Park, Ill. 60085) and which is described in U.S. Pat. No. 6,517,916, the disclosure of which is hereby incorporated herein by reference. Additional layer 52, which may be made of cellulose or another moisture absorbing substance, is bonded to the outside of inner layer 48 by gluing or another bonding technique, as illustrated by bond sites 54. Alternatively, additional layer 52 may be made of any fibrous or non-fibrous material, preferably but not limited to SMS or spun bond polypropylene as discussed in reference to FIGS. 2, 9 and 13-19.

Figure 7:
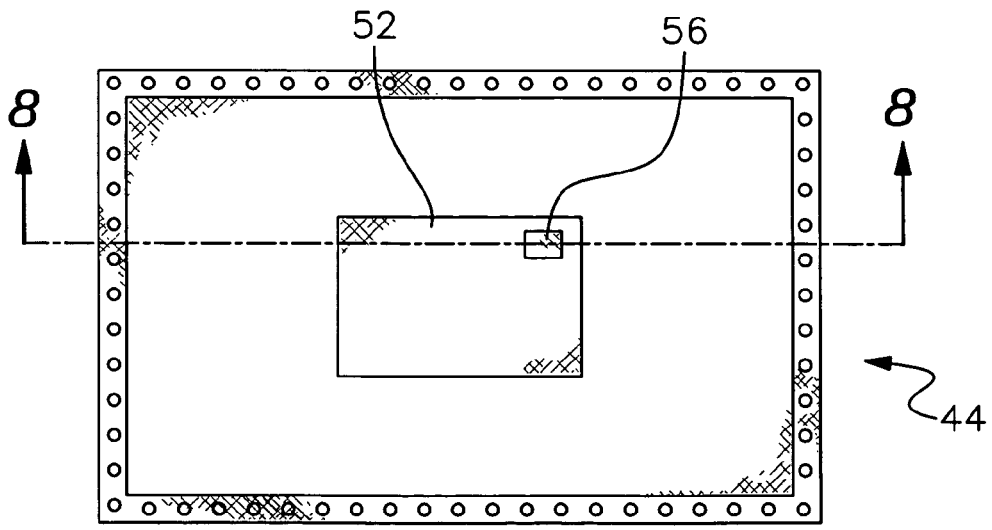
FIG. 7 is a plan view of yet another embodiment of sterilization wrap.
Figure 8:
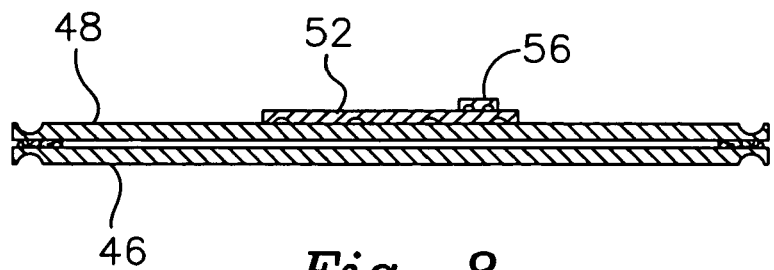
FIG. 8 is a sectional view of the sterilization wrap of FIG. 7 taken through section lines 8-8.

Referring now more particularly to FIGS. 7 and 8, a sterilization indicator device 56 is attached to absorbent layer 52.

Figure 9:
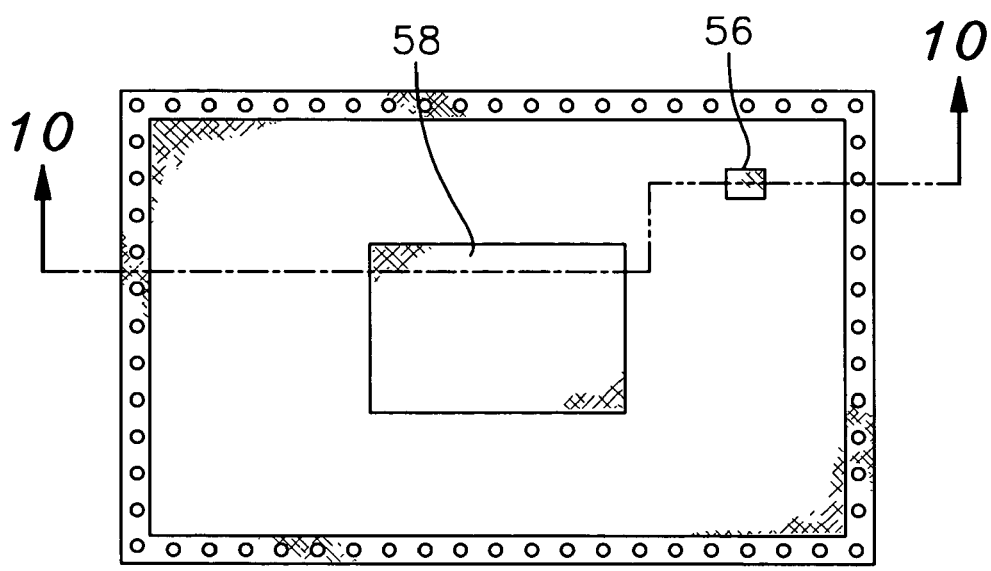
FIG. 9 is a plan view of yet another embodiment of sterilization wrap.
Figure 10:
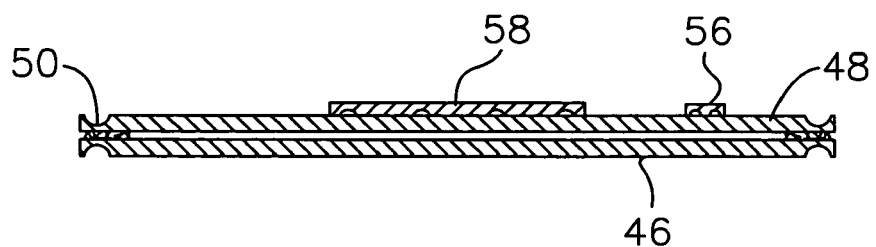
FIG. 10 is a sectional view of the sterilization wrap of FIG. 9 taken through section lines 10-10.

Referring now more particularly to FIGS. 9 and 10, the absorbent layer 52 has been replaced with a reinforcement panel 58 made of either a fibrous or non-fibrous material, preferably but not limited to SMS. Panel 58 has an equal to or higher basis weight than either layer 46 or 48. The basis weight of panel 58 may range from 1.0 ounces per square yard (osy) to 3.0 osy. The basis weight for each of layers 46 and 48 may range from 0.75 osy to 2.9 osy. While reinforcement panel 58 does not provide the moisture wicking function of absorption layer 52, it provides additional protection for the article to be sterilized 36 as shown in FIG. 5, which is to be placed on reinforcement panel 58. The embodiment shown in FIGS. 9 and 10 results in a more cost effective product than the use of two full panels of SMS, but is equal functionally, since less material is used. FIG. 9 also shows a sterilization indicator 56 having been placed on the outside surface of inner panel 48.

Figure 11:
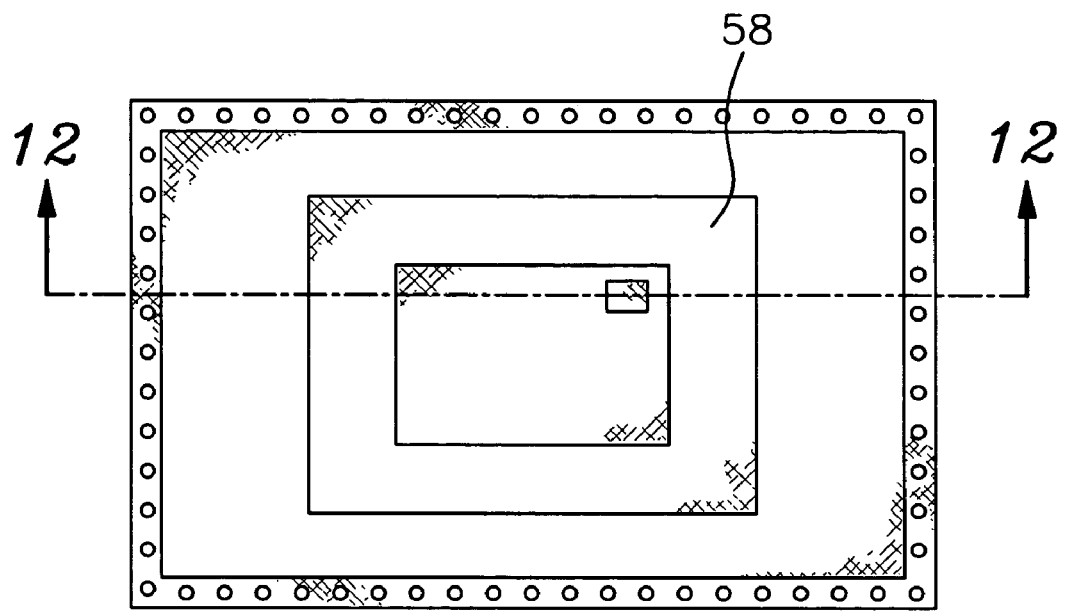
FIG. 11 is a plan view of yet another embodiment of sterilization wrap.
Figure 12:
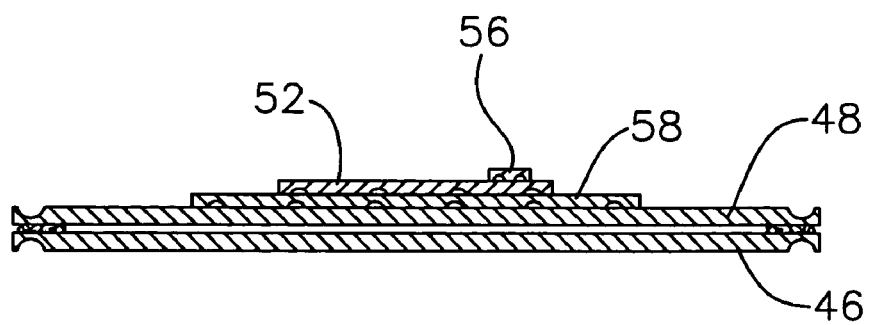
FIG. 12 is a sectional view of the sterilization wrap of FIG. 11 taken through section lines 12-12.
Figure 13:
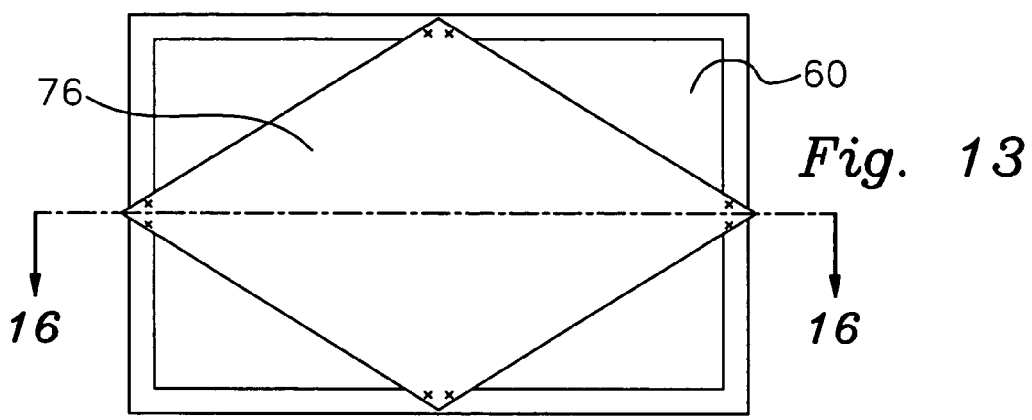
FIG. 13 is a plan view of the preferred embodiment of the invention.

The embodiment of FIGS. 11 and 12 represents a combination of the embodiments of FIGS. 7 and 9. That is, reinforcement panel 58 is attached to inside SMS layer 48. Absorbent layer 52 is, in turn, attached to reinforcement layer 58. Chemical visual indicator 56 is attached to absorbent layer 52. Alternatively, indicator 56 may be attached to reinforcement layer 58 or to inside layer 48. In addition, in the embodiment of FIGS. 11 and 12, outside SMS layer could be eliminated.

Figure 14:
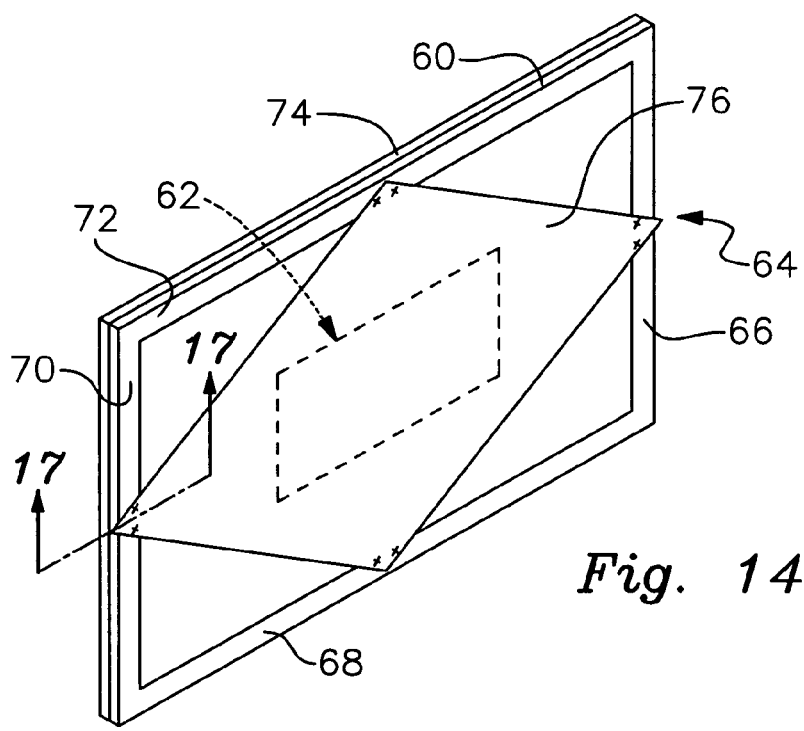
FIG. 14 is a perspective view of the embodiment of FIG. 13.
Figure 15:
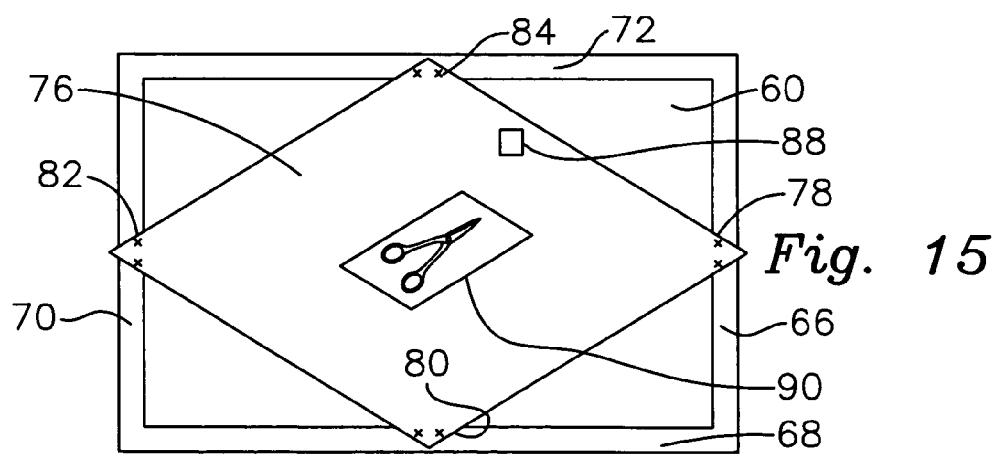
FIG. 15 shows the embodiment of FIG. 13, including the article to be sterilized.
Figure 16:
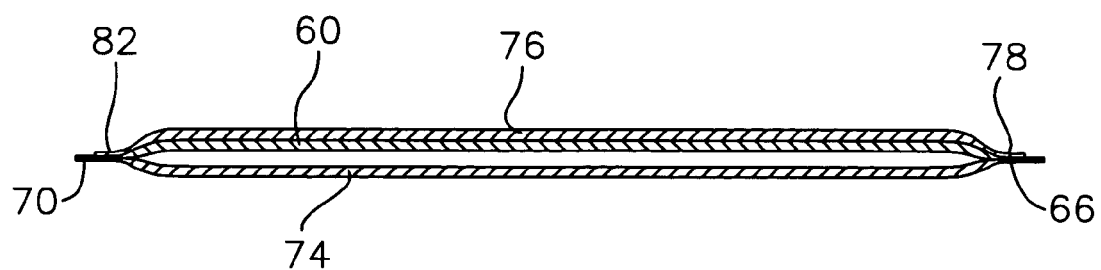
FIG. 16 is a sectional view of the sterilization wrap of FIG. 13 taken through section lines 16-16.
Figure 17:
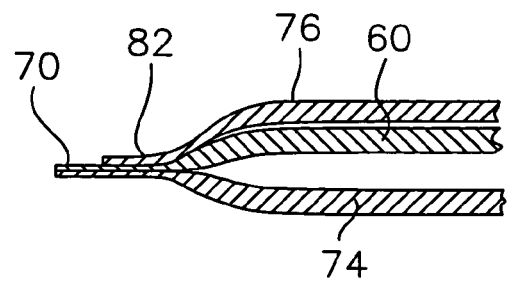
FIG. 17 is a sectional view of the sterilization wrap of FIG. 14 taken through section lines 17-17.
Figure 20:
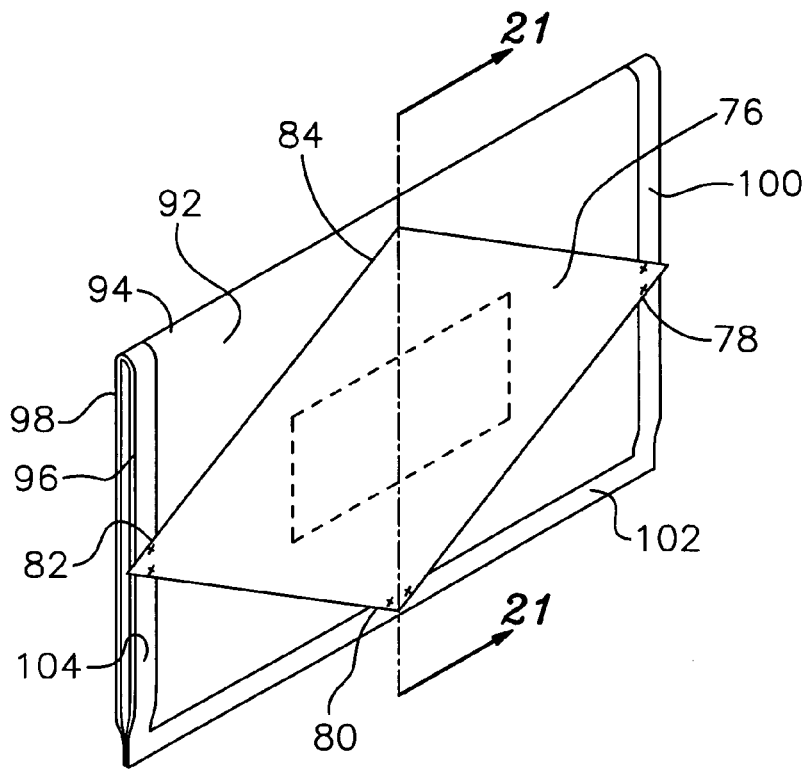
FIG. 20 is a pictorial view of yet another embodiment of the invention.

The embodiment of FIGS. 13-17 represents the preferred embodiment of the invention. A first panel 60 of sterilization wrap is made of sterilization material and preferably includes a layer of pathogen filtration material, such as melt blown polypropylene. Preferably, first panel 60 is made of SMS. First panel 60 includes a central portion generally indicated within the bounds of dashed-lines 62 as shown in FIG. 14. First panel 60 also includes an outer periphery 64. Outer periphery 64 includes four edges 66, 68, 70 and 72. Preferably, a second panel 74 of sterilization wrap is adjacent to and in register with first panel 60. Preferably, the first and second panels are rectangular. In the embodiment of FIGS. 13-17, the first panel 60 of sterilization material is bonded to the second panel 74 of sterilization material along all four edges 66, 68, 70 and 72. The preferred bonding method is ultrasonic bonding. An additional panel 76 is bonded to first panel 60. The additional panel 76 could be made from any fibrous or non-fibrous material. Preferably, the additional panel 76 does not include a pathogen filtration layer and is not made from sterilization material. More preferably, additional panel 76 is made of spun bond polypropylene. Additional panel 76 is oriented so that additional panel 76 forms a diamond pattern with respect to first panel 60. As used herein, "diamond" includes both rhombus and square shapes. Preferably, additional panel 76 is oriented forty-five degrees with respect to first panel 60. A substantial portion of additional panel 76 is adjacent to the central portion 62 of first panel 60. Additional panel 76 is preferably rectangular and includes four corners, namely, corners 78, 80, 82 and 84. In the preferred embodiment all four corners are bonded to first panel 60 as shown in FIG. 15, i.e., corner 78 of additional panel 76 is bonded to edge 66 of first panel 60; corner 80 is bonded to edge 68; corner 82 is bonded to edge 70; and corner 84 is bonded to edge 72. However, as shown in FIG. 20, only three of the edges are bonded to the panel. Preferably, this corner to edge bonding is also accomplished by ultrasonic bonding. As used herein, the term corner includes a region of the additional panel 76 where two of its edges approach one another. The perimeter of additional panel 76 is less than the perimeter of first panel 60.

As shown in FIG. 15, chemical visual indicator 88, which has previously been described, may be attached to additional layer 76. FIG. 15 also illustrates the preferred orientation of the article to be sterilized 90 with respect to additional panel 76 and first panel 60. The protocol for wrapping articles to be sterilized with sterilization wrap is to orient the article at a forty-five degree angle with respect to the first sterilization panel 60. Since, the preferred embodiment calls for the additional panel 76 to be oriented at a forty-five degree angle with respect to the first panel 60, the clinician may place the article to be sterilized with respect to additional panel 76 in alignment with the edges of that panel so that the article will automatically be positioned at a forty-five degree angle with respect to first panel 60.

It is preferred that additional panel 76 has a lower basis weight than first sterilization panel 60 or second sterilization panel 74. Preferably, the basis weight of the additional panel 76 is in the range of 0.5 osy to 3.0 osy. Preferably, the basis weight of each of the first panel 60 and the second panel 74 is in the range of 0.75 osy to 2.9 osy. In addition, it is preferred that the grab tensile to basis weight ratio of additional panel 74 is equal to or greater than the grab tensile to basis weight ratio of the first panel 60.

Preferably, each corner of the additional panel 76 is bonded to the first panel 60 at or about the mid-point of each edge of the first panel 60.

Figure 18:
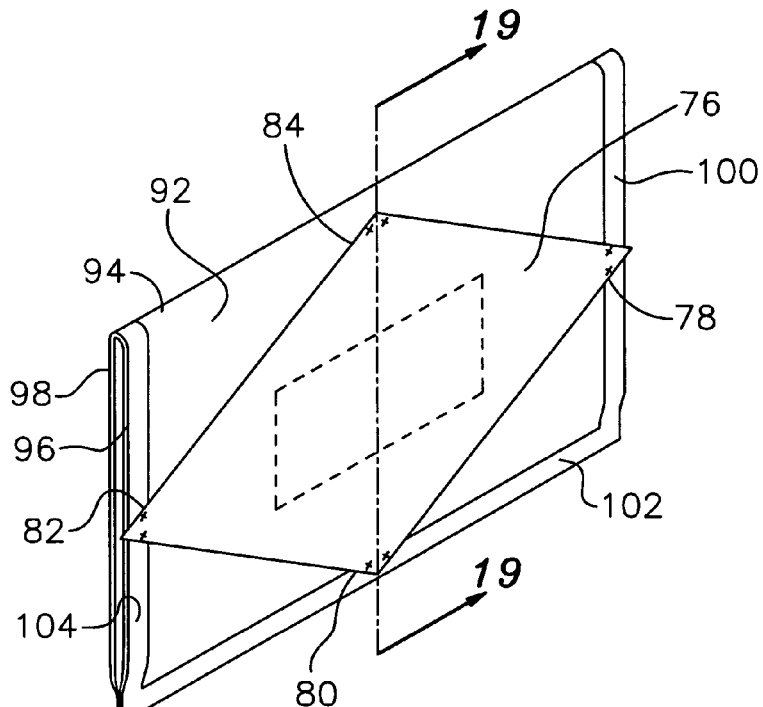
FIG. 18 is a pictorial view of another embodiment of the invention.
Figure 19:
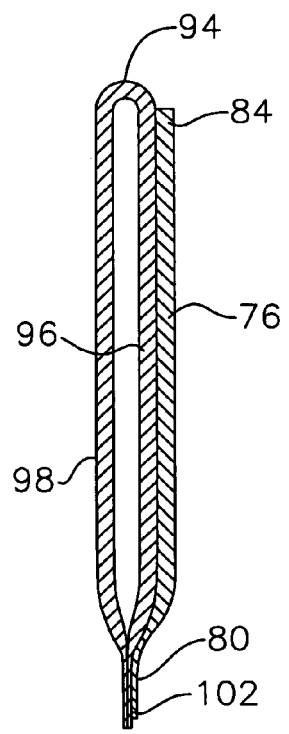
FIG. 19 is a sectional view of the sterilization wrap of FIG. 18 taken through section lines 19-19.

The embodiment of FIGS. 18 and 19 is similar to the embodiment of FIGS. 14-17 except that a single sheet 92 of sterilization material is utilized which is folded in half, as illustrated by fold line 94, to provide two panels of sterilization material 96 and 98. Preferably, only three edges 100, 102 and 104 of the two panels 96 and 98 are bonded together, although these two panels 96 and 98 could also be bonded along fold 94. The corners 78, 80 and 82 of additional panel 76 are bonded to panel 96 along edges 100, 102 and 104. Corner 84 is bonded to panel 96 adjacent to fold 94.

Figure 21:
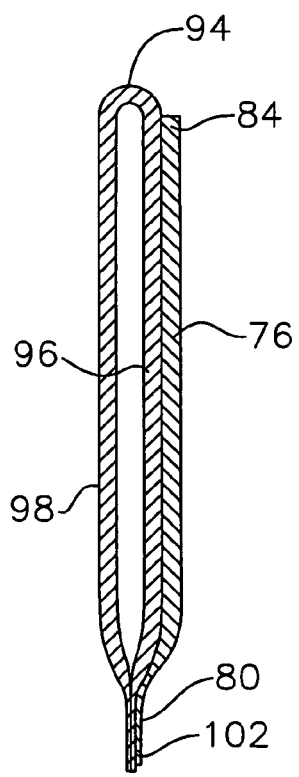
FIG. 21 is a sectional view of the sterilization wrap of FIG. 20 taken through sections lines 21-21.

The embodiment of FIGS. 20 and 21 is identical to the embodiment of FIGS. 18 and 19 except that corner 84 of additional panel 76 is not bonded to panel 96 adjacent to fold 94.

The method for sterilizing article 90 using the sterilization wrap described in reference to FIGS. 13-19 is the same method as described above in reference to the sterilization wrap shown in FIG. 3.

The construction of the sterilization wrap shown in FIGS. 13-19 provides numerous advantages over the prior art. The additional panel 76 made of spun bond polypropylene which is adjacent to the central portion of one of the two SMS panels provides substantial physical protection for the article to be sterilized 90 compared to the prior art two panel SMS product. The additional protection is provided precisely where it is needed, that is, in the central portion 62 where the article to be sterilized is placed. In addition, the forty-five degree orientation of the additional panel 76 with respect to first SMS panel allows the clinician to more readily orient the article to be sterilized 90 in the correct position with respect to the SMS panels.

From the foregoing description of the preferred embodiments of the invention, it is apparent that many modifications may be made therein. It should be understood, however, that these embodiments of the invention are exemplifications of the invention only and that the invention is not limited thereto. It is to be understood, therefore, that it is intended in the appended claims to cover all modifications as fall within the true spirit and scope of the invention.

What is claimed is:

1. A sterilization wrap for wrapping at least one article to be sterilized comprising:
    a first panel of sterilization material; said first panel being rectangular;
    a second panel of sterilization material adjacent to and in register with said first panel;
    an additional panel; said additional panel adapted to receive the article to be sterilized; said additional panel being rectangular; said additional panel being bonded to said first panel; said additional panel being oriented on said first panel so as to form a diamond shape with respect to said first panel; said additional panel being foldable so that said additional panel contacts at least the bottom and sides of the article to be sterilized after wrapping,
    wherein said first and second panels are formed by a single folded sheet of sterilization material; said first panel has first, second, third and fourth edges; said additional panel has first, second, third and fourth corners; and exactly three edges of said first panel are bonded to exactly three corners of said additional panel, and
    wherein said first panel is rectangular and exactly three corners of said additional panel are bonded to respective edges of said first panel approximately at the mid-point of said edges.

2. A sterilization wrap as set forth in claim 1, wherein said second panel of sterilization material is bonded to said first panel of sterilization material.

3. A sterilization wrap as set forth in claim 1, wherein said additional panel is oriented approximately forty-five degrees with respect to said first panel.

4. A sterilization wrap as set forth in claim 1, wherein said additional panel is made of spun bond polypropylene.

5. A sterilization wrap as set forth in claim 1, wherein said first panel is made of SMS.

6. A sterilization wrap as set forth in claim 1, wherein said second panel is made of SMS.

7. A sterilization wrap as set forth in claim 1, wherein said additional panel has a lower basis weight than said first panel.

8. A sterilization wrap as set forth in claim 7, wherein the basis weight of said additional panel is in the range of 0.5 osy to 3.0 osy and the basis weight of said first panel is in the range of 0.75 osy to 2.9 osy.

9. A sterilization wrap as set forth in claim 1, wherein the grab tensile to basis weight ratio of said additional panel is equal to or greater than the grab tensile to basis weight ratio of said first panel.

10. A sterilization wrap as set forth in claim 1, wherein the additional panel is made from cellulose, hydrophilic spun-melt polyolefins, polyester, nylon, polyrayons, bicomponent fibers, spun bond polypropylene, or combinations thereof.

11. A sterilization wrap as set forth in claim 1, wherein said first panel is multi-layered and includes at least one pathogen filtration layer and said additional panel does not include a pathogen filtration layer.

12. A sterilization wrap as set forth in claim 1, wherein said first panel has an outer periphery and a central portion; a substantial portion of said additional panel being adjacent to the central portion of said first panel.

13. A sterilization wrap as set forth in claim 12, wherein the perimeter of said additional panel is smaller than the perimeter of said first panel.

14. A sterilization wrap as set forth in claim 12.

\* \* \* \* \*